United States Patent [19]

Le Van Mao

[11] Patent Number: 4,692,424

[45] Date of Patent: Sep. 8, 1987

[54] DRY IMPREGNATED MANGANESE ZEOLITE

[75] Inventor: Raymond Le Van Mao, Montreal, Canada

[73] Assignee: The Asbestos Institute, Montreal, Canada

[21] Appl. No.: 875,191

[22] Filed: Jun. 17, 1986

Related U.S. Application Data

[63] Continuation-in-part of Ser. No. 688,639, Jan. 3, 1985, Pat. No. 4,615,995.

[51] Int. Cl.$^4$ .......................... B01J 29/28; B01J 21/16
[52] U.S. Cl. ......................................... 502/68; 502/71
[58] Field of Search .............................. 502/68, 71, 77

[56] References Cited

U.S. PATENT DOCUMENTS 4,349,461  9/1982  Chu et al. ............................... 502/77

Primary Examiner—Carl F. Dees
Attorney, Agent, or Firm—Cushman, Darby & Cushman

[57] ABSTRACT

The invention relates to a process for the dry incorporation of manganese ions on the external reactive sites of Zn-ZSM-5 or Zn-ZSM-11 pentasil which comprises mixing a Zn-ZSM-5 or Zn-ZSM-11 zeolite with bentonite, impregnating the dry mixture with a minimum amount of a solution of a manganese salt thereby to form a malleable paste and extruding said paste under pressure whereby the manganese ions are affixed to the surface reactive sites of the treated zeolite and to the zeolite catalyst thus obtained.

2 Claims, No Drawings

DRY IMPREGNATED MANGANESE ZEOLITE

This is a continuation-in-part of U.S. Ser. No. 688,639 filed on Jan. 3, 1985 now U.S. Pat. No. 4,615,995.

DESCRIPTION OF THE PRIOR ART

This invention relates to the incorporation of Mn or other extraneous compounds into zeolites. Zeolites and similar materials have generated considerable interest because of their catalytic properties, in addition to their well-known adsorptive and ion-exchanging capacities.

The so-called shape selectivity in zeolites derives from their regular microporous structures. The zeolite pore size ranges from 3 to 10 angstroms. Due to the pore "narrowness", zeolites can express an effective sieving effect which allows the passage through their pores of only molecules not bulkier than the pore diameter. With zeolites having an average particle size of a few microns, the internal surface area can represent more than 99% of the total surface area. Thus, almost all the active sites are located inside the pores. In many zeolites such as the ZSM-5 zeolite, the size and geometry of the inside of the pores can play a determining role in the reaction mechanism: in fact, the configuration of the reaction intermediates depends on these factors, so does the formation of the final products. As an example, there can be mentioned the methanol conversion to hydrocarbons over ZSM-5 zeolite. After an initial step where methanol is partially converted into dimethyl ether, light olefins (propylene and ethylene) are produced. Then, by a complex sequence of transformations, the light olefins are modified into longer hydrocarbons and finally into aromatics. The loci for such an aromatic formation are said to be the intersections of the ZSM-5 zeolite channels, deeply inside the zeolite particle.

Modifying the reaction sites by incorporation of extraneous compounds or ions can lead to a different product distribution. Zn is known to favor the production of aromatic hydrocarbons: usually, Zn is incorporated by ion-exchange with some of the protonic acid sites; the presence of Zn within the zeolite lattice contributes to increase the production of aromatics in the methanol conversion. Incorporation of Mn, Mg or P into the ZSM-5 zeolite enhances the formation of light olefins: the technique frequently used is known as the wet impregnation process; in the case of P, the product distribution change is due to a P coating of the zeolite particles.

In the common wet impregnation technique, the zeolite particles are completely immersed in a solution which contains an ionic form of the compound to be impregnated. After several hours of such a wet contact, the suspension is evaporated to dryness. With such a technique known as wet impregnation, the compound is deposited randomly inside and outside the zeolite pores. Mn ions deposited by this technique are expected to have some interactions—mostly negative—with the aromatizing active sites.

It would therefore be highly desirable to provide a ZSM-zeolite which would be particularly useful in the conversion of methanol to provide highly desirable yields of both light olefins and aromatic content in the gasoline fraction obtained by the catalytic conversion process.

SUMMARY OF THE INVENTION

In accordance with the present invention, there is now provided a novel and improved zeolite catalyst which is suitable for cracking methanol into high yield of light olefins and aromatics in the gasoline fraction.

The novel zeolite catalyst comprises a Zn-ZSM-5 or Zn-ZSM-11 pentasil zeolite having from 0.1 to 1.0% w/w of zinc ions attached to the internal reaction sites and 0.2 to 5.0% w/w of manganese ions adsorbed on the external reactive sites of the zeolite.

The present invention also provides a new method for depositing the manganese ions on the external reactive sites of a Zn-ZSM-5 or Zn-ZSM-11 pentasil zeolite by a procedure which is referred to as a 'dry process'. Essentially, the novel process of the present invention comprises mixing a zinc containing ZSM-5 or ZSM-11 zeolite with bentonite, impregnating the dry mixture with a minimum amount of a solution of a manganese salt to form a malleable paste and extruding said paste under pressure whereby the manganese ions are affixed to the external surface of the reactive sites of the treated zeolite.

DESCRIPTION OF THE INVENTION

This invention relates to a new technique of Mn incorporation into zeolites known as the dry impregnation technique. The present invention also relates to a new zeolite catalyst onto which Zn and Mn are incorporated, the incorporation of Zn being done by ion-exchange and that of Mn by dry impregnation as mentioned previously. Finally, the present invention provides high yields in light olefins and aromatic hydrocarbons obtained by reacting methanol over the Zn and Mn bearing pentasil-type zeolite, the Zn and Mn being subsequently incorporated with techniques mentioned.

The dry impregnation technique consists of intimately mixing at first the zinc containing zeolite particles with bentonite, then adding dropwise a Mn salt solution to the solid mixture. When the solid mixture turns into a malleable paste, it is pressed into extrudates. This technique ensures that the Mn salt containing solution wets only the external surface of the zeolite particles. In fact, when the Mn solution is added to the bentonite/zeolite solid mixture, the bentonite clay granules which act like a sponge absorb the major part of the Mn solution. The bentonite used in the present preparation can absorb water instantly or can absorb twice its volume of the Mn solution. Then, during the extrusion process where a certain pressure is applied to the paste, a certain amount of the Mn solution is released and thus, wets the exterior of the adjacent zeolite particles. It is worth mentioning that the volume of water or Mn solution required for changing the solid mixture into a malleable paste is very low.

When a ZSM-5 zeolite (under acid form) is submitted to an ion-exchange with Zn and the Zn-ZSM-5 zeolite thus obtained is subjected to a dry impregnation with Mn, the resulting catalyst provides an unexpectedly higher production of light olefins and aromatics in the methanol conversion to hydrocarbons. This is a really unexpected result because a Zn and Mn bearing ZSM-5 zeolite prepared in the same way excepted for the Mn incorporation by the common wet impregnation technique, produces more light olefins than the parent zeolite but does not give such a high increase in aromatic yield as the catalyst where Mn was incorporated by the impregnation technique of the present invention.

It should be appreciated that in an industrial conversion of methanol (or alcohol) to hydrocarbons by a process using a pentasil-type zeolite as catalyst, product liquid hydrocarbons which ranges from $C_5$ to $C_{11}$ are obtained and these may be advantageously used as gasoline. One of the parameters which contributes to enhancing the octane number of such a gasoline is the aromatic content. Thus, a difference of 15 to 20% points in the aromatic content of the gasoline can represent significant earnings without involving any additional production costs.

EXPERIMENTAL

For comparative purpose, the following three catalysts were prepared:
 (1) pure ZSM-5 zeolite based, labeled "ZSM-5";
 (2) Zn-Mn bearing ZSM-5 zeolite where Zn had been incorporated into the ZSM-5 zeolite by ion-exchange and Mn had been subsequently incorporated by the wet impregnation technique. This sample was labeled "ZSM-5/ Zn-Mn(W)";
 (3) Zn-Mn bearing ZSM-5 zeolite where Zn had been incorporated into the ZSM-5 zeolite by ion-exchange and Mn had been subsequently incorporated by the dry impregnation technique of the present invention. This sample was labeled "ZSM-5/Zn-Mn(D)".

(A) Preparation and characterization of the catalysts
ZSM-5 sample:

This sample was prepared according to the following procedure (see also: R. J. Argauer and G. R. Landolt, U.S. Pat. No. 3702886, Example 27; R. Le Van Mao et al., Canadian Journal of Chemistry, Vol. 63(12), 3464, 1985, section "Preparation of the catalysts"):

25 g of Silica Baker (>90% Silica by weight) were suspended in a solution prepared from 40 g of tetrapropylammonium bromide and 2.5 g of NaOH dissolved in 140 ml of distilled water. The suspension was heated at 80° C. under vigorous stirring for 1 hour. Then, a solution prepared from 1.8 g of sodium aluminate (Fisher, % weight composition: alumina =46.79; sodium oxide =28.44) dissolved in 20 ml of distilled water, was added. Heating was continued at 80° C. with vigorous stirring for 10 minutes. The suspension was transferred into a Hastelloy C container which was then put into a Parr autoclave, and heated for 10 days at 170° C. (±5° C.). After cooling, the suspension was discharged and filtered; the solid was washed with distilled water until the washing liquid had a pH lower than 9 and then dried at 120° C. for 12 hours and activated in the air at 550° C. for 12 hours (weight of the resulting solid: 22.8 g).

20 g of the solid previously obtained were brought in contact with an aqueous solution of ammonium chloride at 5% by weight, using 10 ml of solution per gram of compound. The suspension was heated at 80° C. under reflux condition and with moderate stirring. After 1 hour of heating, the suspension was allowed to settle and the liquid was then rapidly removed. A fresh volume of ammonium chloride solution was added and the suspension was heated again for another hour. The same procedure was repeated several times so that the entire operation lasted 5 hours. The suspension was filtered and the solid was washed until $Cl^-$ ions were no longer present in the washings. The compound was dried at 120° C. for 12 hours and activated in the air for 12 hours at 550° C.

The resulting material (acid form or H-form) had the following chemical composition (% by weight): silica =97.7, alumina =2.1 and sodium oxide =0.2 (Si/Al molar ratio =40).

The degree of crystallinity which was determined according to the method of Le Van Mao et al (Canadian Journal of Chemistry, Vol. 63(12), 3464, 1985, section "X-ray powder diffraction") was DC =95%.

The final catalyst was prepared according to the following procedure: the previously obtained solid was intimately mixed with bentonite (35% by weight) and made into pastes with distilled water, 1 ml of water was used for each gram of the solid. The pastes were pressed into 1 mm O.D. extrudates. Finally, the extrudates were dried at 120° C. for 12 hours and activated in the air at 550° C. for 12 hours. This sample was called "ZSM-5".

Zn loading:

The Zn loading onto the ZSM-5 (H-form) sample was done according to the following procedure:

8 g of "ZSM-5" were brought in contact with an aqueous solution of $ZnCl_2$ (Mallinckrodt) at 2% by weight, using 80 ml of solution as total volume of $ZnCl_2$ solution. The suspension was heated at 80° C. under reflux and with moderate stirring. After 3 hours of heating, the suspension was cooled down, then filtered and washed with distilled water until $Cl^-$ ions were no longer present in the washings. The compound was dried at 120° C. for 12 hours and activated in the air at 550° C. for 12 hours. The Zn metal content was 0.55 wt% by weight. This material was called "ZSM-5/Zn".

ZSM-5/Zn-Mn(D):

This sample was prepared starting from the "ZSM-5/Zn" material and following the "dry" impregnation technique as described below:

1.9 g of "ZSM-5/Zn" were intimately mixed with 0.7 g of bentonite and made into pastes with 2.0 ml of an aqueous solution of $MnCl_2$ [5 wt% in water]. The pastes were pressed into 1 mm O.D. extrudates. Finally, the extrudates were dried at 120° C. for 12 hours and activated in the air at 550° C. for 12 hours. This sample was called "ZSM-5/Zn-Mn(D)" and its metal Mn content was 2.2 wt%.

ZSM-5/Zn-Mn(W):

This sample was prepared according to the well-known "wet" impregnation method, also taught by Chu and Kaeding [Example 1 of U.S. Pat. No. 4349461]. The preparation was as follows:

3 g of "ZSM-5/Zn" were added to 7 ml of a $MnCl_2$ aqueous solution [1.2 g of $MnCl_2$ dissolved in 50 ml of water]. The suspension was allowed to stand overnight at ambient temperature, then the water was evaporated in an oven. The resulting material was activated in the air at 550° C. for 12 hours. The final form of this sample was obtained by extruding with bentonite (35 wt%) in presence of water as described in the preparation section of the ZSM-5. The metal Mn content of this sample was 1.5 wt%.

(B) Catalytic testing

The obtained samples in bead form and having a density of 0.48 g/cubic cm were tested in the following reaction system:

Catalytic runs were performed by injecting methanol using an injection syringe on an infusion pump into a methanol vaporizer gas mixer. Nitrogen gas was supplied to the methanol vaporizer and gas mixer from a cylinder connected in-line with a flowmeter. The vaporized methanol was then carried by the nitrogen gas through a catalyst bed set in a catalytic reactor contained inside an oven which was thermo-regulated. A chromel-alumel thermocouple was placed in the catalyst bed and was used, in conjunction with a digital thermometer unit, to monitor the temperature of the catalyst bed. The gaseous mixture flowing out of the catalytic reactor was run through a series of condensers maintained at 5°-10° C., to a liquid collector immersed in an ice bath followed by a cylinder from which gas sampling was carried out. Following a pre-run of 10 minutes, the liquid products were collected and the gaseous ones were analyzed periodically by gas chromatography using a 3.5 m long column packed with Chromosorb P coated with 20% by weight of Squalane. The GC used was a dual FID Hewlett-Packard Model 5790 equipped with a 3392A Model integrator. It was equipped also with a capillary column (length: 50 m; PONA type fused silica coated with a cross-linked polymer) which was used for accurate analyses of the liquid fractions after a run was completed. The composition of the aqueous layer was also determined by GC using a methanol in water calibration standard.

The reaction conditions used in the experiments were as follows:

Temperature =400° C.; nitrogen flow rate =10 ml/mn; WHSV (weight hourly space velocity) =2.2 $h^{-1}$; duration of the experiment =4 hours (under methanol stream); methanol injected =15.6 g; weight of catalyst loaded in the (quartz) reactor =circa 1.8 g.

Three catalytic runs were performed with each sample. The reported yields and product distributions were averaged values of data from these runs. Reaction temperatures and flow rates were carefully and automatically controlled. As a consequence, no difference in the catalytic data higher than 5% was observed with the same catalyst tested under the same reaction conditions.

Catalytic results are reported in Table 1.

Table 1 reports the product yields obtained with the ZSM-5 zeolite and with catalysts modified by subsequent incorporation of Zn and Mn, the latter metal ion having had been incorporated by both impregnation techniques. A sharp increase in the formation of light olefins and a slight but significant increase in the production of liquid hydrocarbons ($C_5$ to $C_{11}$, i.e. the gasoline boiling range hydrocarbons) were observed with both samples. However, an unexpected increase in the aromatic content of the liquid hydrocarbons was obtained with the ZSM-5/Zn-Mn(D) sample. Such an hydrocarbon liquid if used as gasoline did have much higher octane number rating than the liquid produced by the sample prepared by the Mn wet impregnation technique.

Moreover, the incorporation of Zn and Mn (by the dry impregnation technique of the present invention) led to sharp yield increases in the BTX aromatics (Benzene, toluene, ethylbenzene and xylenes) and particularly, in the xylenes (see Table 1). It is worth mentioning that such aromatic compounds have a wide range of applications in the petrochemical and chemical industries.

Regardless to the possible use of the liquid hydrocarbon as gasoline, gasoline blending stock or chemical feedstocks, high yields in the most commercially valuable products (light olefins and aromatics) represent a true profit advantage for an industrial process mostly when no change in the reaction parameters are needed, i.e. no additional production costs are required. Similar results are obtained when Zn-ZSM-5 is replaced by Zn-ZSM-11.

What is claimed is:

1. A process for the dry incorporation of manganese ions on the external reactive sites of Zn-ZSM-5 or Zn-ZSM-11 pentasil which comprises mixing a Zn-ZSM-5 or Zn-ZSM-11 zeolite with bentonite, impregnating the dry mixture with a minimum amount of a solution of a manganese salt thereby to form a malleable paste and extruding said paste under pressure whereby the manganese ions are affixed to the surface reactive sites of the treated zeolite.

2. The process of claim 1, wherein the starting zeolite is Zn-ZSM-5.

TABLE 1

PRODUCT YIELDS IN THE METHANOL CONVERSION TO HYDROCARBONS

| CATALYST | Zn content (wt %) | Mn content (wt %) | Yield in kg per 100 kg of methanol | | | Characteristics of the $C_5$-$C_{11}$ (liquid) hydrocarbons | | | |
|---|---|---|---|---|---|---|---|---|---|
| | | | $C_1$-$C_4$ Paraffins | $C_2$-$C_4$ Olefins | $C_5$-$C_{11}$ (liquid) hydrocarbons | Aromatic content (wt %) | Octane rating (1) | BTX (2) content (wt %) | Xylenes (3) content (wt %) |
| ZSM-5 | — | — | 12.4 | 6.4 | 18.8 | 35 | low | 23 | 13 |
| ZSM-5/Zn—Mn (W) | 0.55 | 1.5 | 4.6 | 14.1 | 19.4 | 40 | low | 23 | 18 |
| ZSM-5/Zn—Mn (D) | 0.55 | 2.2 | 6.8 | 13.3 | 20.2 | 55 | high | 34 | 27 |

(1) qualitative assessment for comparison purpose only (in case of use as gasoline)
(2) benzene + toluene + ethylbenzene + xylenes
(3) para + ortho + meta - xylenes

* * * * *